(12) United States Patent
Lalena

(10) Patent No.: US 8,961,011 B2
(45) Date of Patent: Feb. 24, 2015

(54) MOBILE RADIOGRAPHY UNIT HAVING MULTIPLE MONITORS

(75) Inventor: Michael C. Lalena, Webster, NY (US)

(73) Assignee: Carestream Health, Inc., Rochester, NY (US)

(*) Notice: Subject to any disclaimer, the term of this patent is extended or adjusted under 35 U.S.C. 154(b) by 415 days.

(21) Appl. No.: 13/084,831

(22) Filed: Apr. 12, 2011

(65) Prior Publication Data

US 2012/0093298 A1    Apr. 19, 2012

Related U.S. Application Data

(60) Provisional application No. 61/323,473, filed on Apr. 13, 2010.

(51) Int. Cl.
*H05G 1/02*    (2006.01)
*H05G 1/00*    (2006.01)
*A61B 6/00*    (2006.01)

(52) U.S. Cl.
CPC ............. *A61B 6/4405* (2013.01); *A61B 6/464* (2013.01); *A61B 6/465* (2013.01); *A61B 6/467* (2013.01)
USPC ........... 378/198; 378/98.5; 378/197; 378/204

(58) Field of Classification Search
CPC ..................... G05B 2219/13144; A61B 5/743; A61B 5/7435; A61B 5/7475; A61B 5/748
USPC ............. 378/62, 91, 98, 98.5, 98.8, 189, 193, 378/194, 197, 198, 204, 210
See application file for complete search history.

(56) References Cited

U.S. PATENT DOCUMENTS

| | | | |
|---|---|---|---|
| 5,844,961 A | 12/1998 | McEvoy et al. | |
| 6,256,374 B1* | 7/2001 | Tomasetti et al. | 378/98.2 |
| 7,481,578 B2* | 1/2009 | Chapman | 378/197 |
| 7,611,282 B2 | 11/2009 | Koren et al. | |
| 2007/0273697 A1* | 11/2007 | Zaman et al. | 345/501 |
| 2008/0147398 A1* | 6/2008 | Kagermeier et al. | 704/246 |

FOREIGN PATENT DOCUMENTS

| | | |
|---|---|---|
| WO | 2007/078684 | 7/2007 |
| WO | 2007/139638 | 12/2007 |

* cited by examiner

*Primary Examiner* — Anastasia Midkiff

(57) ABSTRACT

A mobile radiography apparatus has a moveable (e.g., wheeled) transport frame and an adjustable column mounted at the frame. A boom apparatus supported by the adjustable column can support an x-ray source and can be coupled to a second display (also adjustably mounted). The second display and a first display can each be configured to control the mobile radiography apparatus and display items such as but not limited to (a) obtained images and/or related data or (b) a control panel to allow functions such as generating, storing, transmitting, modifying, and printing of the obtained images.

20 Claims, 13 Drawing Sheets

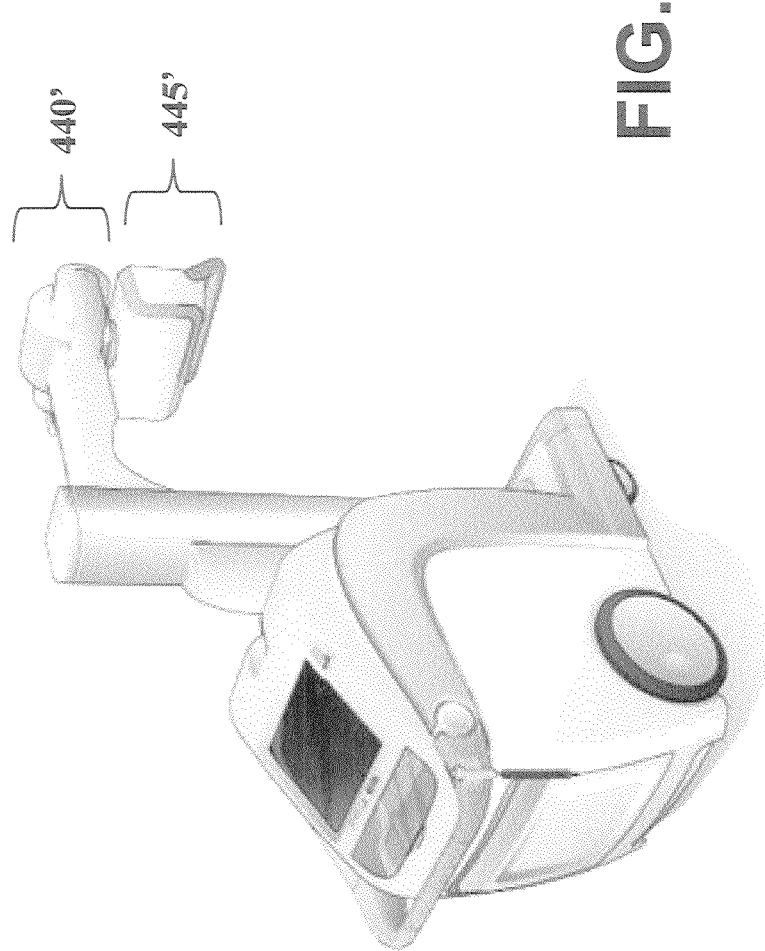

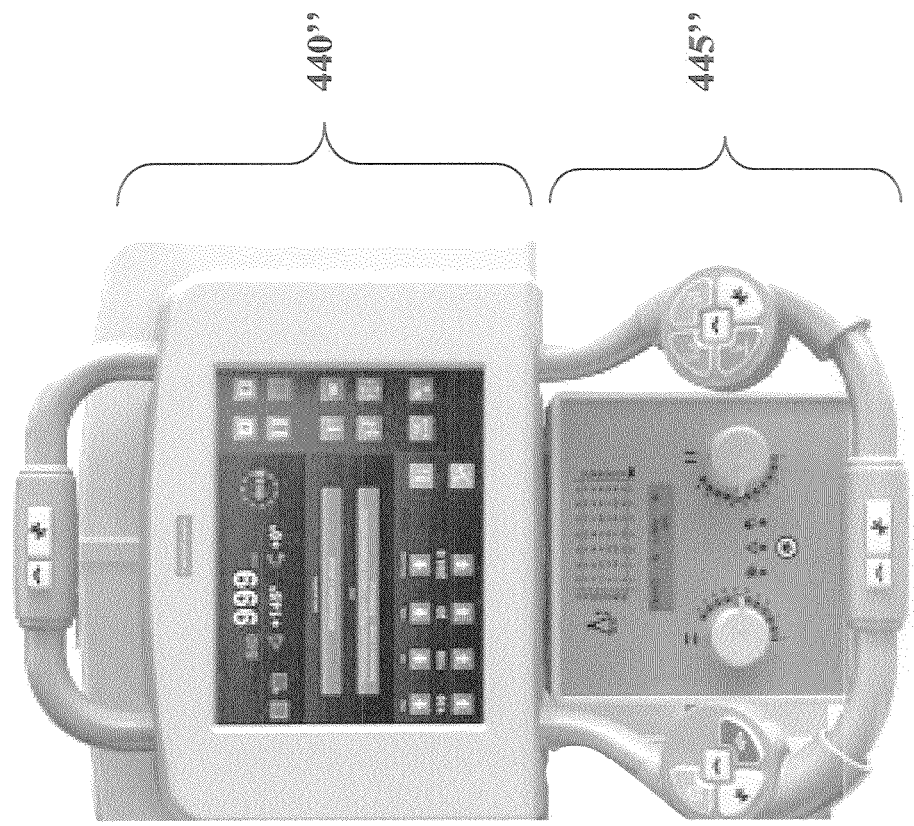

| Patient Name | Location | Exam | Exam Time |
|---|---|---|---|
| James Johnson | Rm 203 | Portable Chest | 4/11/2010 11:23:51 AM |
| Fred Smith | Rm 224 | Knee | 4/11/2010 11:24:12 AM |
| Fred Jones | Rm 245 | Portable Chest | 4/11/2010 11:23:44 AM |
| Scott Smith | Rm 252 | Portable Hip | 4/11/2010 11:24:05 AM |
| John Jones | Rm 483 | Portable Hip | 4/11/2010 11:22:48 AM |
| Bill Miller | Rm 508 | Portable Hip | 4/11/2010 11:23:37 AM |
| Bill Smith | Rm 572 | Knee | 4/11/2010 11:23:30 AM |
| Bill Miller | Rm 778 | Portable Chest | 4/11/2010 11:23:16 AM |
| Mike Jones | Rm 884 | Knee | 4/11/2010 11:23:23 AM |
| Robert Jones | Rm 944 | Portable Hip | 4/11/2010 11:23:02 AM |
| Fred Johnson | Rm 993 | Knee | 4/11/2010 11:23:58 AM |

New Exam Requested

Exam Time: 4/11/2010 11:25:01 AM

Location: Rm 816

Patient Name: Mark Bailey

Exam: Portable Hip

Routine

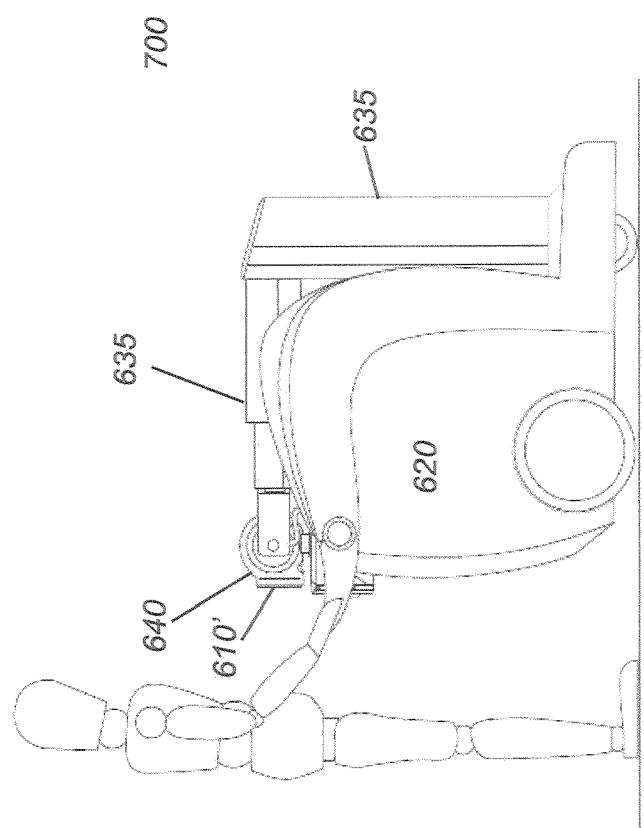

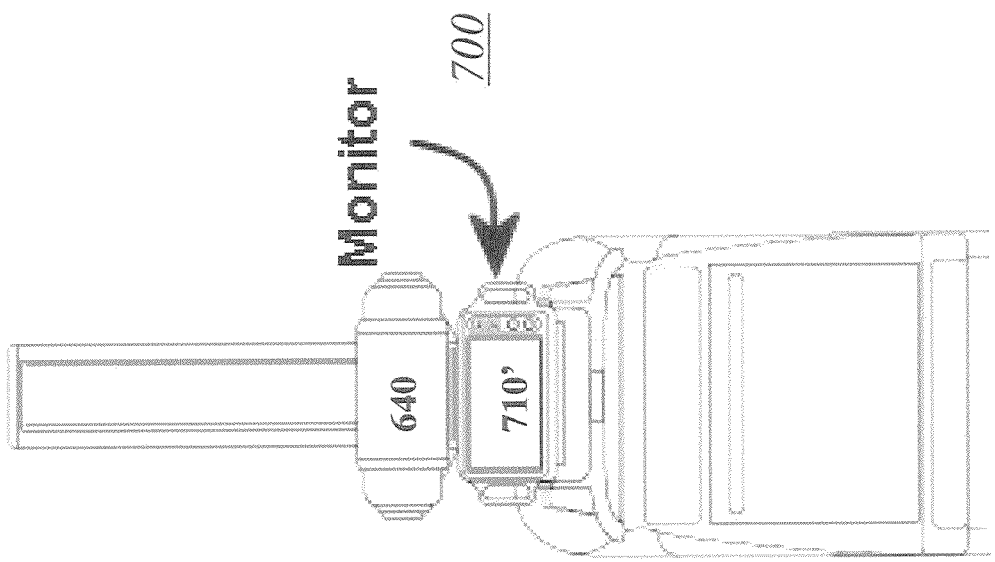

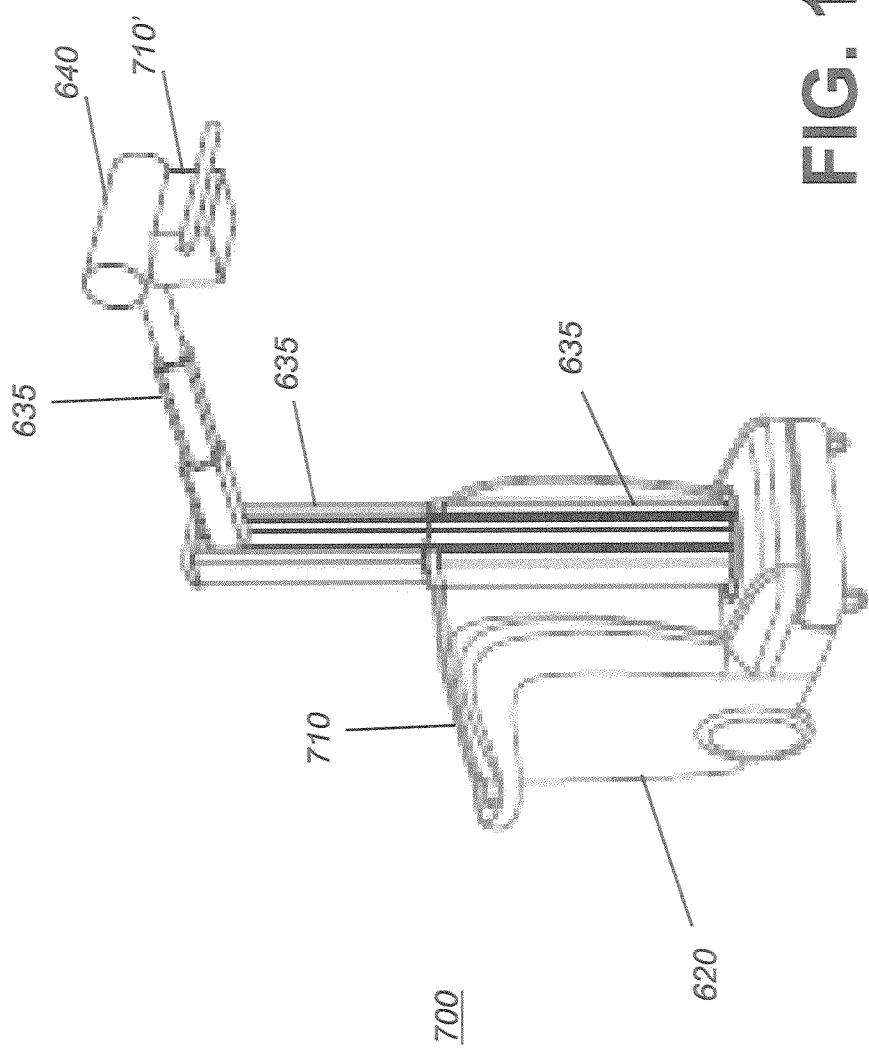

MOBILE RADIOGRAPHY UNIT HAVING MULTIPLE MONITORS

CROSS REFERENCE TO RELATED APPLICATIONS

Priority is claimed from commonly assigned, U.S. provisional patent application Ser. No. (a) 61/323,473, filed Apr. 13, 2010, entitled "MOBILE UNIT HAVING DISPLAY", in the name of Michael C. Lalena, the disclosure of which is incorporated by reference.

FIELD OF THE INVENTION

The invention relates generally to the field of medical imaging, and in particular to portable radiographic imaging apparatus. More specifically, the invention relates to a mobile radiography apparatus having multiple displays/controls or a display/console mounted to an adjustable radiation source support structure.

BACKGROUND

Mobile carts are employed in medical facilities to move medical equipment between locations. One type of mobile cart includes an x-ray source used to capture (e.g., digital) x-ray images on x-ray detector. Medical x-ray images can be captured using various techniques. For example, techniques such as computed radiography (CR) and digital radiography (DR) can be used to obtain medical images.

Refer also to U.S. Pat. No. 7,611,282 (Koren) and WO 2007/139638 (Jadrich), and WO 2007/078684 (Dhurjaty), and U.S. Pat. No. 5,844,961 (McEvoy).

Mobile x-ray apparatus are of particular value in intensive care unit (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

However, there is a need for improvements in mobile x-ray apparatus design to allow such devices to be more easily transported, deployed and/or operated.

SUMMARY OF THE INVENTION

An aspect of this application is to advance the art of mobile radiography.

Another aspect of this application to address in whole or in part, at least the foregoing and other deficiencies in the related art.

It is another aspect of this application to provide in whole or in part, at least the advantages described herein.

Another aspect of the application is to provide methods and/or apparatus by which mobile radiography carts can be modified to use a plurality of displays/monitors/controllers.

Another aspect of the application is to provide methods and/or apparatus by which mobile radiography carts can use a display/monitor/controller mounted to an adjustable support structure for an x-ray source.

Another aspect of the application is to provide a mobile x-ray system having a display at a mobile transport frame and another display mounted to an adjustable support structure for a tube head or the tube head. In one embodiment, the tube head can include an x-ray source and a collimator.

In accordance with one embodiment, the present invention can provide a mobile radiography apparatus that can include a moveable transport frame; a handle coupled to the moveable transport frame; an adjustable support structure coupled to the moveable transport frame; an x-ray source; and a display to provide control of the x-ray source, where the display and the x-ray source are mounted to the adjustable support structure.

In accordance with one embodiment, the present invention can provide a method for mounting a second display for use at a portable x-ray radiography apparatus, the method can include providing a moveable transport frame; coupling a first tube head support structure to the moveable transport frame; coupling a second adjustable tube head support structure to the first tube head support structure; coupling a the tube head to the second adjustable tube head support structure; and coupling a second display to the second adjustable tube head support structure, the second display to provide control of an x-ray source.

In accordance with one embodiment, the present invention can provide a mobile radiography apparatus that can include a moveable transport frame; a first display at the transport frame; an adjustable mount structure coupled to the movable transport frame; and a tube head mounted to the adjustable mount structure, the tube head can include a portion of the adjustable mount structure, an x-ray source, and second display.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 5 is a diagram that shows a perspective view of another embodiment of a display/monitor as a second display mounted to a boom assembly of a mobile radiography unit according to the application.

FIG. 6 is a diagram that shows an embodiment of a display/monitor as a second display mounted to a tube head of a mobile radiography unit according to the application.

FIGS. 7-10 are diagrams that illustrate exemplary functions implemented at an embodiment of a second display of a mobile x-ray imaging apparatus.

FIGS. 11A-11C are diagrams that show another exemplary embodiment of a mobile radiographic imaging apparatus including more than a single display/operator console positioned for transport or use, respectively.

DESCRIPTION OF EXEMPLARY EMBODIMENTS

Figure 1:
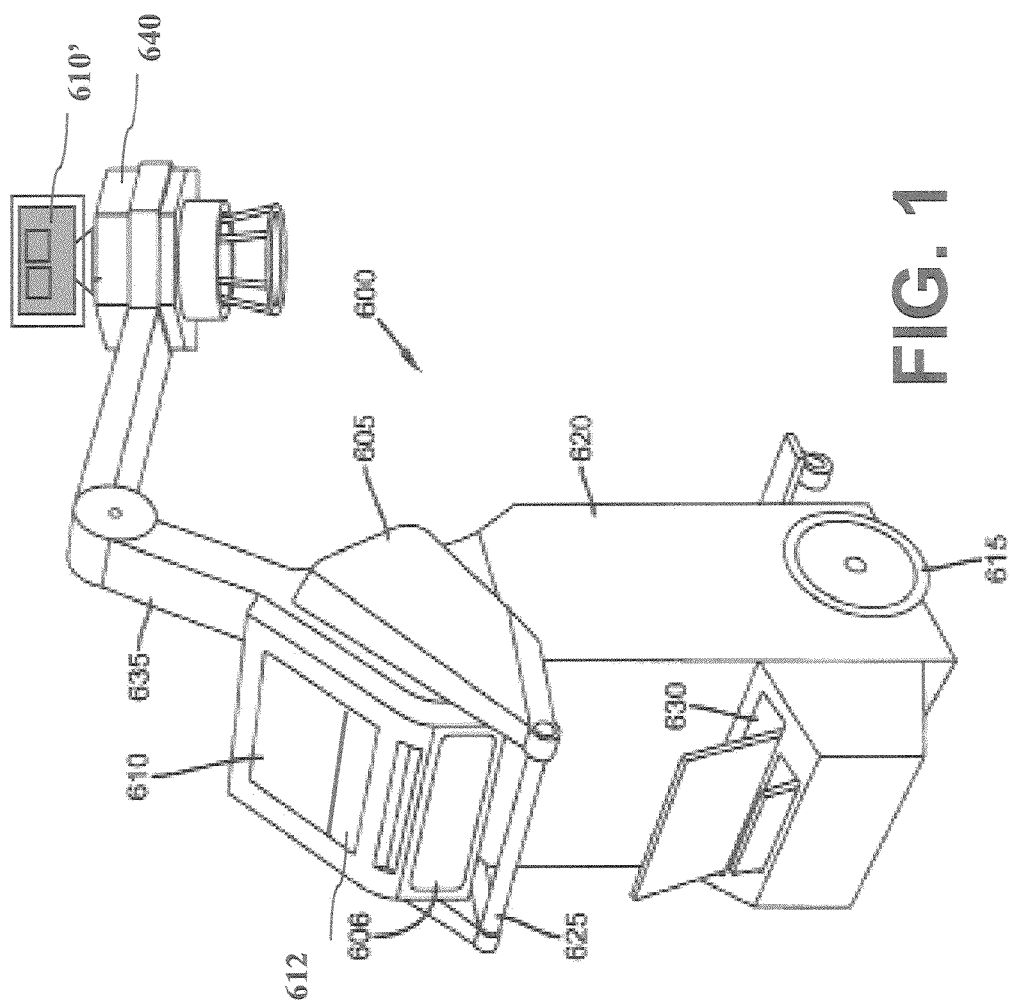
FIG. 1 is a diagram that shows a perspective view of a mobile radiography unit with a second display according to one embodiment of the application.

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

FIG. 1 is a diagram that shows a perspective view of a mobile radiography unit with a second display according to one embodiment of the application. The exemplary mobile x-ray or radiographic apparatus of FIG. 1 can be employed for x-ray film, computed radiography (CR) and/or digital radiography (DR). As shown in FIG. 1, a mobile radiography apparatus 600 can include a moveable transport frame 620 that includes a first display 610 for display of obtained images and related data. The first display 610 can implement or control functions such as generating, storing, transmitting, modifying, and printing of an obtained image(s). Alternatively, the first display 610 can include an integral or separate control panel 612 to assist in implementing functions such as generating, storing, transmitting, modifying, and printing of an obtained image(s).

For mobility, the mobile radiographic apparatus 600 has one or more wheels 615 and one or more handle grips 625, typically provided at waist-, arm-, or hand-level, that help to guide the mobile radiographic apparatus 600 to its intended location. The mobile radiographic apparatus 600 can include a self-contained battery pack (e.g., rechargeable) typically provides source power, which can reduce or eliminate the need for operation near a power outlet. Further, the self-contained battery pack can provide for motorized transport. Alternatively, the mobile radiographic apparatus 600 can exclude a battery pack to be operated only when connected to an external power source like an AC power supply or plugged into a power outlet. When used for computed radiography (CR), the mobile radiographic apparatus 600 can include optional CR scanner 605 having an opening 606 into which the cassette can be inserted.

For storage, the mobile radiographic apparatus 600 can include an area/holder for holding/storing one or more digital detectors or computed radiography cassettes. The area/holder can be storage area 630 (e.g., disposed on the frame 620) configured to removably retain at least one digital radiography (DR) detector. The storage area 630 can be configured to hold one or more detectors and can also be configured to hold one size or multiple sizes detectors.

Mounted to frame 620 is a support column 635 that supports an x-ray source 640, also called an x-ray tube or tube head that can be mounted to the support column 635. In the embodiment shown in FIG. 1, the support column 635 can include an articulated member that bends at a joint mechanism to allow movement of the x-ray source 640 over a range of vertical and horizontal positions. In another embodiment, the tube head or x-ray source 640 can be rotatably coupled to the support column 635. In another exemplary embodiment, the support column 635 can include a second section that extends outward a fixed/variable distance from a first section where the second section is configured to ride vertically up and down the first section to the desired height for obtaining the image. Height settings for the x-ray source 640 can range from low height for imaging feet and lower extremities to shoulder height and above for imaging the upper body portions of patients in various positions. In exemplary embodiments, the support column 635 (e.g., and/or tube head) can allow 1 degree of freedom, two degrees of freedom, or 3 degrees of freedom for the x-ray source 640 relative to the frame 620. Further, the x-ray source 640 can be mounted directly to support member 635 by a flexible or bendable arm such that the x-ray source is can be rotated about one or more axis.

The exemplary mobile radiographic apparatus 600 can include a second display/monitor 610' coupled to a tube head or x-ray source 640. As shown in FIG. 1, the second display 610' can be pivotable mounted above the x-ray source 640 to be viewable/touchable from a 360 degree area around the tube head.

Figure 2:
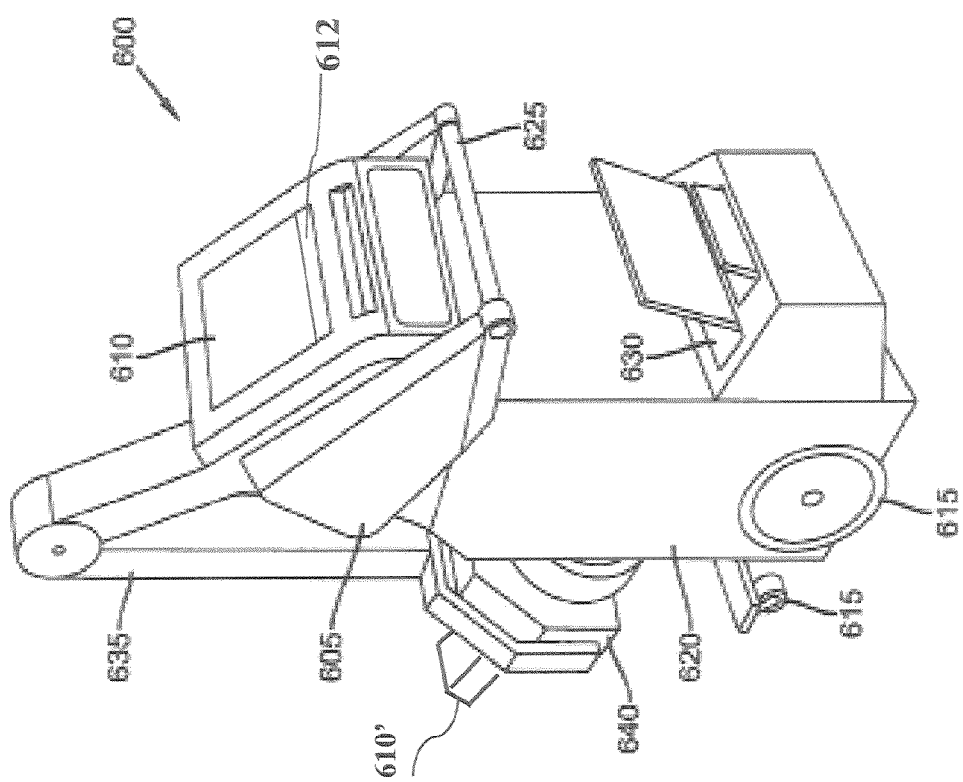
FIG. 2 is a diagram that shows a perspective view of a mobile radiography unit of FIG. 1 positioned for travel.

As shown in FIG. 2, for ease during transport of the mobile radiographic apparatus 600, the support member 635 and x-ray source 640 can be arranged close to frame 620. As shown in FIG. 2, the second display 610' can be moved from a first position (e.g., upright) to a second position (e.g., substantially flat) for additional protection during transport of the mobile radiographic apparatus 600. When the mobile radiographic apparatus 600 is to be used, the support member 635 and x-ray source 640 can be extended from the frame 620 for proper positioning (e.g., by the operator, a user, or x-ray technician) and the second displayed moved to the first position as shown in FIG. 1.

Figure 3:
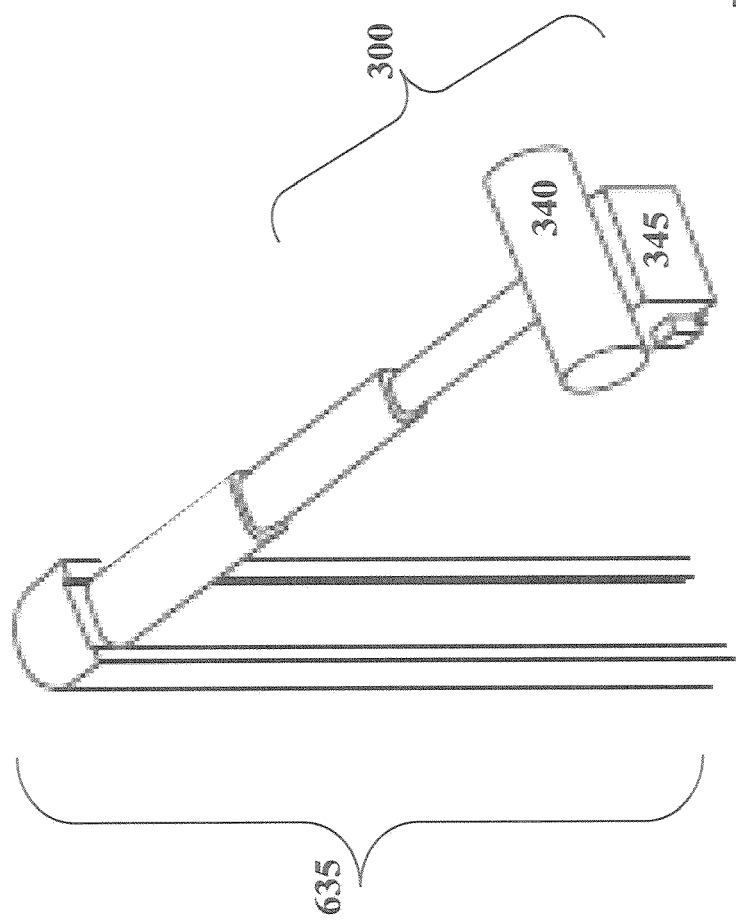
FIG. 3 is a diagram that shows a perspective view of an embodiment of a boom assembly to support a second display of a mobile radiography unit according to the application.

FIG. 3 is a diagram that shows a perspective view of an embodiment of a boom assembly to support a second display of a mobile radiography unit according to the application. As shown in FIG. 3, a "boom assembly" such as boom assembly 300 can refer to the x-ray tube, a housing for the x-ray tube 340, a collimator 345, a structure/box below the collimator 345 used to achieve (for example, 30 cm) separation between the tube and the patient, or any portion of the adjustable support column 635 that can be used to position the tube over the patient.

Figure 4:
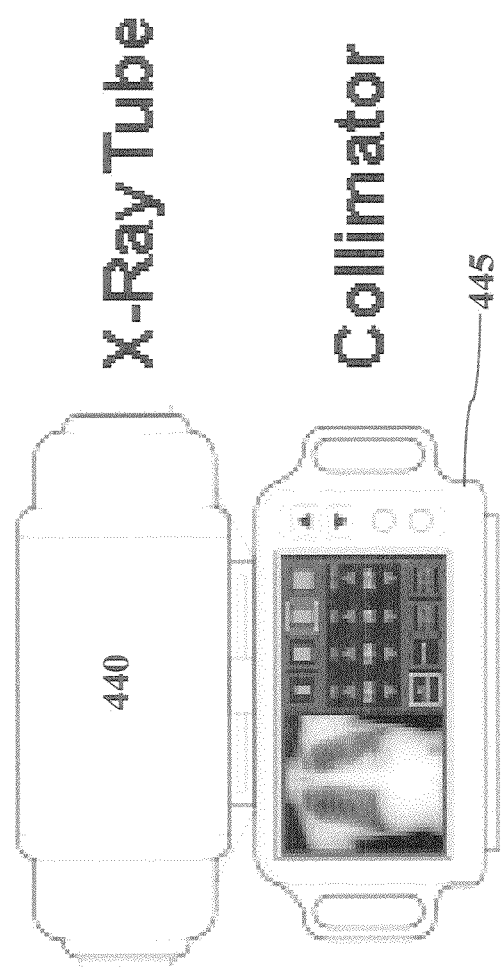
FIG. 4 is a diagram that shows an embodiment of a display/monitor as a second display mounted to a boom assembly of a mobile radiography unit according to the application.

FIG. 4 is a diagram that shows an embodiment of a display/monitor as a second display mounted to a boom assembly of a mobile radiography unit according to the application. As shown in FIG. 4, the second display 610' can be mounted to a collimator 445 of an x-ray source 440 of a boom assembly of a mobile radiography unit. In one embodiment, the collimator 445 is rotably mounted to the x-ray source 440 so that the collimator 445 (e.g., second display 610') can swivel at least 90 degrees, at least 180 degrees or 360 degrees. As shown in FIG. 4, the second display 610' is coupled to a plurality of handles for ease of positioning.

FIG. 5 is a diagram that shows another embodiment of a display/monitor as a second display mounted to a boom assembly of a mobile radiography unit according to the application. As shown in FIG. 5, the second display 610' can be mounted to a collimator 445' of an x-ray source 440' of a boom assembly of a mobile radiography unit. As shown in FIG. 5, the second display 610' can use a single lower handle for ease of positioning (e.g., 3D positioning relative to a patient and independent adjustment of the second display).

FIG. 6 is a diagram that shows yet another embodiment of a display/monitor as a second display mounted to a boom assembly of a mobile radiography unit according to the application. As shown in FIG. 6, the second display 610' can be mounted to an x-ray source 440" above a collimator 445" of a boom assembly of a mobile radiography unit. In FIG. 6, the second display 610' could be mounted for independent adjustment relative to the collimator 445" or the x-ray source 440".

Conventional mobile x-ray apparatus can include a main console (e.g., single display) on the transport frame to control operations of the mobile x-ray apparatus and/or to view images captured using the x-ray source of the conventional mobile x-ray apparatus. However, when positioning a conventional mobile x-ray apparatus, for example in an intensive care room/operation or emergency situation, the technician may not have the time to move between a first location (e.g., patient side or bedside) where the technician positions the x-ray source (or tube head) and a second location where the technician can view the information at the main console on the transport frame of the conventional mobile x-ray apparatus. Further, the patient and/or an x-ray detector such as a wireless flat panel detector can move from the arrangement preset by the technician for exposure while the technician moves from the first position to the second position for viewing the information/control the exposure at the main console. In addition, some patient care procedures require additional medical personnel who can be around the patient during x-ray operations and can be inconvenienced or forced into improper caretaking positions while the technician moves from the first position to the second position at the main console on the conventional mobile x-ray apparatus.

Embodiments of mobile x-ray apparatus and/or methods for using the same can use a second display mounted to/located at an x-ray source, a tube head, a boom assembly or a support column so that the technician can position a mobile x-ray apparatus (e.g., boom assembly) for an exposure, view the information on the second display and/or operate the mobile x-ray apparatus (e.g., x-ray tube) using the second display from a single location (e.g., without moving).

According to exemplary embodiments of the application, the second display 610' can provide information such as but not limited to: (i) general information such as date, time, environment conditions, and the like; (ii) unit information such as model serial number, operating instructions, warning information, and the like; (iii) patient data, such as patient name, room number, age, blood type, and the like; (iv) indicators such as but not limited to cart power/battery indicators, detector status (e.g., on/off), wireless signal strength/connectivity, grid alignment aides, cart diagnostics and/or (v) imaging/procedure information, such as the exam type, exposure information, and the like.

In one embodiment, the second display 610' can provide a back-up mode or "fail safe mode" so that in the event of a failure of the first display 610 or the console/PC/processor, which can control the first display 610, the second display 610' can operate to change exposure parameters and/or expose CR cassettes or expose x-ray film cassettes in the back-up mode. Thus, the mobile radiographic apparatus 600 can perform x-ray exposures when either one of the first display 610 or the second display 610' are inoperable.

Figure 9:
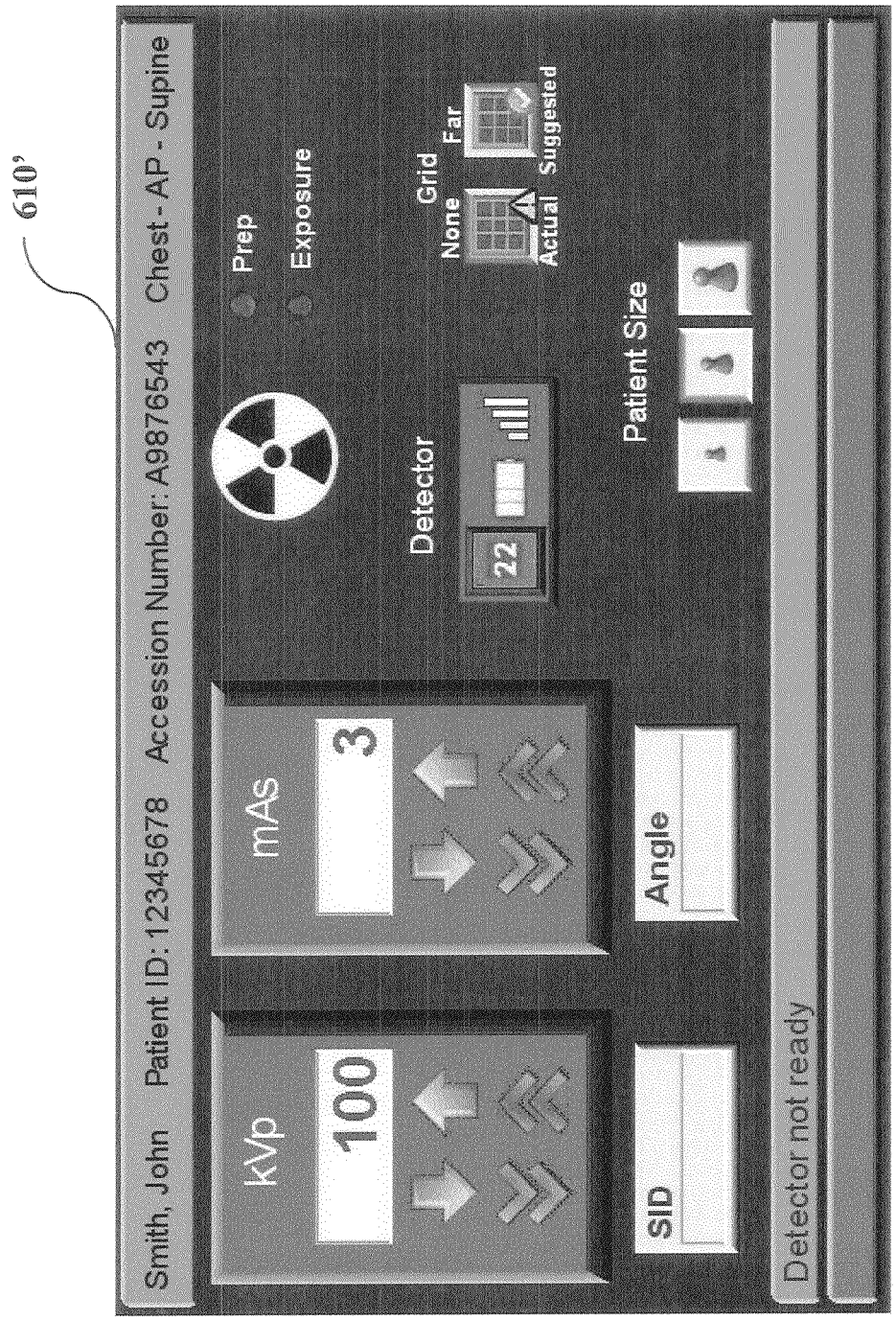
Figure 10:
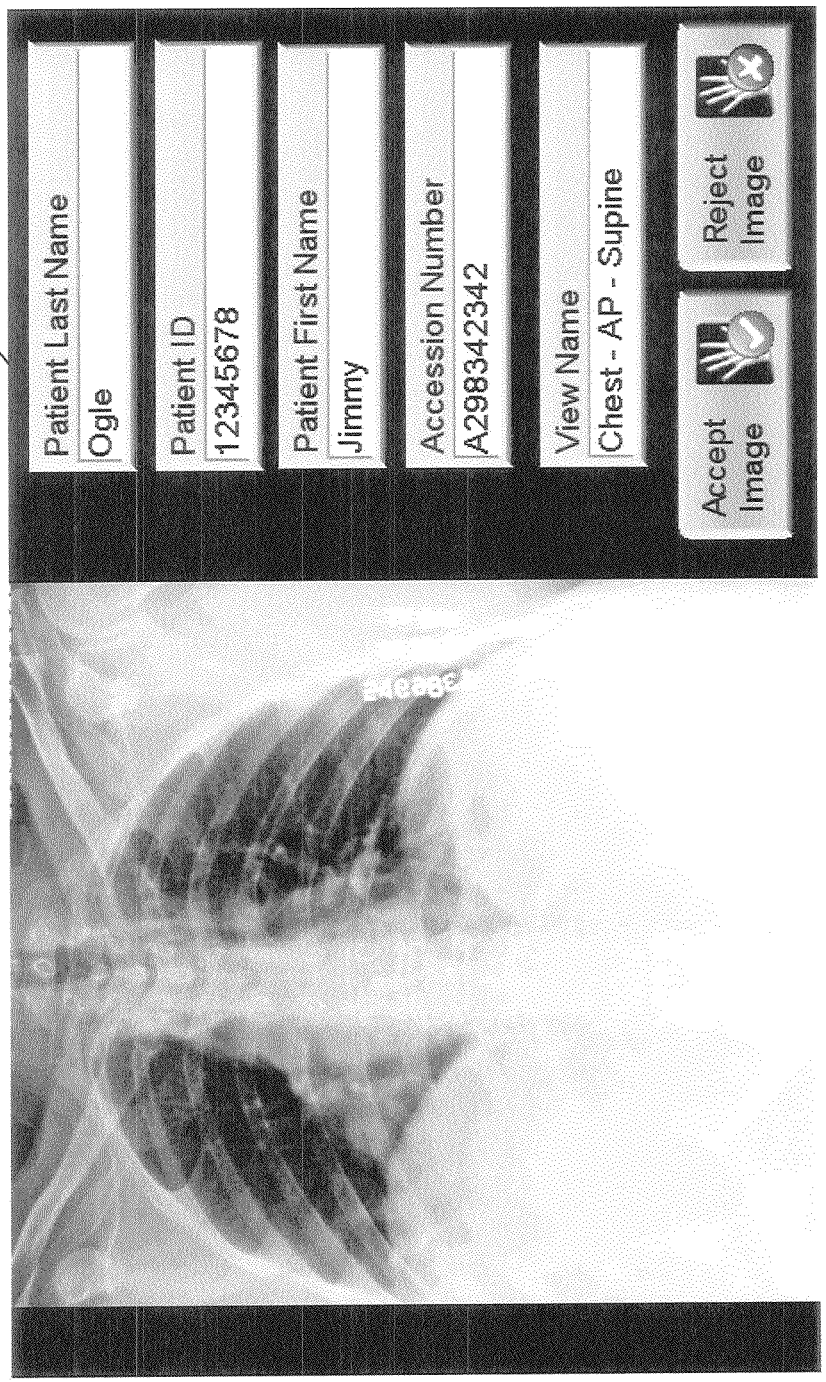

FIGS. 7-10 are diagrams that illustrate exemplary non-limiting representative functions illustrated on an embodiment of a second display of a mobile e-ray imaging apparatus. As shown in FIG. 7, an example of a work list is shown on a monitor of the second display 610'. As shown in FIG. 8, an example of a new examination/procedure information/requirement for that technician and/or patient is shown on a monitor of the second display 610'. As shown in FIG. 9, an example of x-ray source controls is shown on a monitor of the second display 610'. As shown in FIG. 10, an example of newly acquired (or prior) image and patient information is shown on a monitor of the second display 610'.

In one embodiment, the first display 610 can implement a subset of the functionality of the second display 610'. In another embodiment, the second display 610' can implement a subset of the functionality of the first display 610. Alternatively, information and controls capable of use at the first display 610 can be provided (e.g., identically) at the second display 610'. In one embodiment, the second display 610' can include one or more handles for positioning the tube head or adjustable support column 635 and/or the second display 610'.

According to embodiments of the application, the second display 610' can provide capabilities/functionality to the mobile x-ray imaging apparatus 600 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm that the correct patient); (iv) display and/or change a Patient Worklist, such as a list of exams to perform and allow the user to select an exam (In one embodiment, such a patient worklist can be automatically updated (e.g., synchronized to a master/hospital/doctor worklist) using a wired or wireless network/connection. In one embodiment, the mobile x-ray imaging apparatus 600 can highlight/indicate new exams (e.g., on the second display 610') upon receipt of the scheduled examination.); (v) display generator/source current values and controls to change those values, such as: kVp, mA, mAs, Time, ECF, focal spot, collimator, filter, AEC, grid; (vi) display detector selection and allow the technician to select/activate a different detector; (vii) display recently acquired images and allow editing of those images, exemplary acquired (e.g., recently) or previous images can be displayed full size, partial size or with corresponding image information; (viii) display previously acquired images (e.g., related prior images of a patient) and allow editing of those images; or (ix) display a video of what is in front of the mobile x-ray imaging apparatus 600 during transport, e.g., using a video camera located on the other side (e.g., front side of the mobile x-ray imaging apparatus 600).

In one embodiment, the second display 610' and/or the first display 610 can be actuated for example using an attached keyboard/mouse, a remote control, a touch screen, a tethered control, an operable screen or the like.

In one embodiment, the second display 610' and/or the first display 610 can be configured to rotate (e.g., automatically) a user interface display thereon to match a portrait orientation or a landscape orientation based on positioning by the operator (e.g., a rotation/orientation of the long/short side) of the second display 610' and/or the first display 610. In one embodiment, the operator can controllably select (e.g., force) one of the portrait orientation or the landscape orientation for the user interface at the second display 610' and/or the first display 610.

In one embodiment, the second display 610' and/or the first display 610 can operate in a display synchronization mode where a first display user interface is synchronized to or concurrently displays (e.g., matches) the same user interface that is displayed at a second display user interface. Further, in the display synchronization mode, when one of the first display user interface or the second display user interface is, the other of the first display user interface and the second display user interface is concurrently modified to match. Thus, in the display synchronization mode, the operator can move between the first display 610 and the second display 610' and always find the identical display/user interface available, which can ease operation of a portable radiographic imaging apparatus including two displays.

For example, when the tube head is locked or docked in a travel configuration, the operator can view a worklist on the second display 610', select a patient from the worklist and navigate to that selected patient's scheduled examination. While the tube head is docked, the first display 610 is preferably turned off. Then, when the tube head is unlocked and the first display 610 is revealed in the display synchronization mode, the first display 610 is enabled and showing that selected patient's scheduled examination.

FIGS. 11A-11C are diagrams that show another exemplary embodiment of a mobile radiographic imaging apparatus including more than a single display/operator console. As shown in FIGS. 11A-11C, a mobile radiographic imaging apparatus 700 can include a first display 710 and a second display 710' mounted to the adjustable support column 635 (e.g., tube head).

In the embodiments shown in FIGS. 11A-11C, the mobile radiography unit 700 has a wheeled transport frame 620 and has display and control panel components needed for operation, as was described previously with reference to FIG. 1. As shown in FIG. 11A and FIG. 11C, the adjustable support column 635 can include a sectioned vertical column with two movable sections, a first, top movable section labeled a and a second, middle movable section (e.g., movable in telescoping fashion with respect to a stationary base section). A horizontal boom can extend outward from the sectioned vertical column and can be rotated into position about a vertical axis. In one embodiment, both rotation about vertical axis V and vertical displacement along the vertical axis can be performed simultaneously.

In a travel configuration of FIG. 11A, the adjustable support column 635 has the sectioned vertical column collapsed and the boom is rotated inward in order to seat x-ray source 640 in a stable position for movement, such as for wheeling from one patient area to another. FIG. 11C shows the adjustable support column 635 with the vertical column fully extended, with the boom facing outward and with movable sections at an extended position.

In one embodiment, the second display 710' can also provide for visibility for seeing in front of the mobile radiographic imaging apparatus 700. In some situations, the adjustable support member 635 supporting the x-ray tube/collimator can be an obstruction when an operator is pushing/moving the mobile radiographic imaging apparatus 700. FIG. 10B shows a back side view (e.g., head on) of the mobile radiographic imaging apparatus 700 configured for travel with x-ray source 640 adjacent a top surface of the transport frame. To address such a condition an/or to improve visibility during travel, the mobile radiographic imaging apparatus 700 can include a video/camera or other capture device positioned on the apparatus 700 opposite the handle or positioned to view an area in front of the apparatus 700. The adjustable support member 635 supporting the second display 710' on the tube/tube head can be configured such that a display/monitor of the second display 710' can be visible to the operator standing by the handle. An image and/or video captured by the capture device can be displayed on the second display 710' at the tube head whereby the operator pushing/moving the mobile radiographic imaging apparatus 700 during travel can "drive" the mobile radiographic imaging apparatus 700 by looking at the second display 710'.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Embodiments according to the application can provide various advantages including a mobile x-ray unit including a display/monitor mounted to/on the collimator, x-ray tube head, generator, or any part of the boom assembly or a mobile x-ray unit including two displays for control of the unit.

Through the use of a second display mounted to a column or adjustable column, which can be operatively coupled to a camera or video camera that can preferably face forward during transport, exemplary apparatus and methods embodiments according to the present application can further address the need for a radiography unit that can be readily wheeled from one place to another within a treatment facility, without the physical or visual obstruction that is common to many types of conventional mobile radiography equipment that use a vertical column.

In one embodiment, the mobile radiographic imaging apparatus can be operated/controlled by programmed control logic in the first or second displays. For example, the programmed control logic can include a processor and display, an integrated computer system, or a portable computer and applications to operate thereon.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A mobile x-ray radiography apparatus comprising:
   a moveable transport frame;
   a handle coupled to the moveable transport frame;
   an adjustable support structure coupled to the moveable transport frame;
   an x-ray source; and
   a first display to provide control of the x-ray source, where the first display and the x-ray source are mounted to the adjustable support structure, where the first display is configured to display currently acquired medical radiographic images of the mobile x-ray radiography apparatus or prior patient medical radiographic images, and where the first display implements complete x-ray exposure control and operational control for the mobile x-ray radiography apparatus.

2. The apparatus of claim 1 where the adjustable support structure comprises a tube head, where the tube head comprises the x-ray source and the first display.

3. The apparatus of claim 2 comprising a second display mounted to the moveable transport frame, where the second display is configured to provide control of the x-ray source.

4. The apparatus of claim 3 where the adjustable support structure is configured to be adjustable in two dimensions or adjustable in three dimensions relative to the moveable transport frame, where the first display is rotatable in a horizontal plane, rotatable in a vertical plane or rotatable both horizontally and vertically, and where the first display pivotably mounted to the adjustable support structure and can swivel at least 90 degrees or the first display is rotatable around the tube head or the adjustable support structure.

5. The apparatus of claim 3, where the first display is configured to implement a subset of the functionality of the second display, the second display is configured to implement a subset of the functionality of the first display or the second display is configured to implement the functionality of the first display.

6. The apparatus of claim 3, comprising a display synchronization mode where of the first display user interface is configured to match a second display user interface, and where when one of the first display user interface and the second display user interface is changed in the display synchronization mode, the other of the first display user interface and the second display user interface is modified to match.

7. A method for mounting a second display for use at a portable x-ray radiography apparatus, the method comprising:
  providing a moveable transport frame to include a first display, the moveable transport frame configured to transport the radiography apparatus;
  coupling a first tube head support structure to the moveable transport frame;
  coupling a second adjustable tube head support structure to the first tube head support structure;
  coupling a tube head to the second adjustable tube head support structure; and
  coupling a second display to the second adjustable tube head support structure, the second display to provide control of an x-ray source, wherein the first display and the second display are respectively configured to display currently acquired medical radiographic images of the mobile x-ray radiography apparatus or prior patient medical radiographic images when the first and second tube head support structures are not in a docked travel configuration, and wherein the first display is turned off, the second display is turned on, and the second display at least partially obscures the first display when the first and second tube head support structures are docked in a travel configuration.

8. The method of claim 7, where the second display is configured to display a video of an area in front of the portable x-ray radiography apparatus during transport of the portable x-ray radiography apparatus, comprising coupling an additional adjustable tube head support between the first tube head support structure and the second adjustable tube head support structure.

9. A mobile x-ray radiography apparatus comprising:
  a moveable transport frame, the moveable transport frame configured to transport the mobile x-ray radiography apparatus;
  a first display at the transport frame;
  an adjustable mount structure coupled to the movable transport frame; and
  a tube head mounted to the adjustable mount structure, the tube head comprising:
    a portion of the adjustable mount structure, and
    a second display,
  wherein the second display is configured to be operable and the first display is configured to be inoperable when the adjustable mount structure is docked in a travel configuration during transport of the mobile x-ray radiography apparatus from a first x-ray exposure operation location to a second x-ray exposure operation location.

10. The apparatus of claim 9, where the first display and the second display are each configured to display obtained images and related data and a control panel to allow functions including storing, transmitting, modifying, and printing of the obtained images.

11. The apparatus of claim 9, where the adjustable mount structure comprises a telescoping structure, a telescoping adjustable structure, a structure adjustable in two dimensions or a structure adjustable in three dimensions, where the second display is rotatably physically mounted to the tube head, where the second display is rotatable by a swivel mount, where the second display is rotatably mounted by a flexible arm or swivels on a positionable arm.

12. The apparatus of claim 9, where the tube head comprises a collimator and an x-ray source, where the second display is mounted to the collimator or the x-ray source, where the second display is rotatable relative to the collimator or the x-ray source, where the second display is rotatable relative to the adjustable mount structure.

13. The apparatus of claim 9, where the second display can be physically detached from the tube head and comprises a wireless or physical communication link for use between the second display and the tube head.

14. The apparatus of claim 9, wherein the movable transport frame is a wheeled transport frame, where the mobile x-ray radiography apparatus is configured to provide simultaneous vertical, horizontal and rotational movement of the second display relative to the moveable transport frame, where the first display and the second display are each configured to control an exposure by the x-ray source.

15. The apparatus of claim 9, where the first display and the second display are each configured to view and/or modify x-ray exposure parameters, view and/or modify generator/source/technique settings, display image information, display patient information, display a patient worklist, display generator current values and controls to change those values, display detector selection, allow the user to select/activate a different detector, display recently acquired images and allow editing of those images, indicators or imaging procedure information.

16. The apparatus of claim 9, where the second display is configured to display a video of an area in front of the mobile x-ray radiography apparatus during transport of the mobile x-ray radiography apparatus.

17. The apparatus of claim 9, where the first display is configured to implement a subset of the functionality of the second display, the second display is configured to implement a subset of the functionality of the first display or the second display is configured to implement the functionality of the first display.

18. The method of claim 7, further comprising:
  displaying a patient worklist during the transport of the mobile x-ray radiography apparatus on the second display.

19. The method of claim 7, further comprising:
  displaying cart power/battery indicators or wireless signal strength/connectivity during the transport of the mobile x-ray radiography apparatus on the second display.

20. The apparatus of claim 9, where the second display is configured to provide a back-up mode to control exposure parameters in the event of the first display or console failure.

* * * * *